United States Patent [19]
Galen et al.

[11] Patent Number: 6,128,530
[45] Date of Patent: Oct. 3, 2000

[54] FAIL-SAFE DEFIBRILLATOR

[75] Inventors: Peter Galen, McMinnville, Oreg.; William E. Saltzstein, Woodinville, Wash.

[73] Assignee: Agilent Technologies, Inc., Santa Clara, Calif.

[21] Appl. No.: 09/195,072

[22] Filed: Nov. 18, 1998

[51] Int. Cl.$^7$ .................................................. A61N 1/39
[52] U.S. Cl. ............................................................. 607/5
[58] Field of Search ............................................ 607/4–8

[56] References Cited

U.S. PATENT DOCUMENTS

| | | | |
|---|---|---|---|
| 5,464,435 | 11/1995 | Neumann | 607/9 |
| 5,496,349 | 3/1996 | Campbell et al. | 607/5 |
| 5,571,141 | 11/1996 | McNeil et al. | 607/5 |
| 5,607,455 | 3/1997 | Armstrong | 607/8 |
| 5,674,252 | 10/1997 | Morgan et al. | 607/5 |
| 5,683,423 | 11/1997 | Post | 607/5 |
| 5,733,309 | 3/1998 | Kroll et al. | 607/5 |

*Primary Examiner*—William E. Kamm

[57] ABSTRACT

A defibrillator having one or more redundant systems each including functionally interchangeable components from which one component is selected for current operation. Manual or automatic selection of one component in each redundant system is made to form an operational defibrillator. Preferably, such selection is based on a real-time evaluation of the operational integrity of all operational components in a redundant system. Such real-time evaluations may be performed by monitoring systems within a controller, by an external test system within or external to the defibrillator or by self-test mechanisms internal to the operational components themselves. Factors such as user preferences, default component assignment, and predetermined arrangements of operational component combinations may be included in the selection determination along with the operational integrity of each operational component. If certain, non-critical components fail with no functionally interchangeable components available, then the redundant system comprising such a failed component is not made operational. The remaining systems of the defibrillator may still be implemented to form a defibrillator sufficient for defibrillation yet lacking the capability to implement the functions allocated to the malfunctioning, degraded or otherwise absent redundant system.

20 Claims, 6 Drawing Sheets

FAIL-SAFE DEFIBRILLATOR

BACKGROUND OF THE INVENTION

1. Field of The Invention

The present invention relates generally to a portable external defibrillator and, more particularly, to a portable external defibrillator having redundant components to enable continued operation of defibrillator.

2. Related Art

Sudden cardiac arrest is a disruption of the heart's functioning that causes a lack of blood flow to vital organs. In a majority of instances, sudden cardiac arrest is manifested as an abnormal or chaotic heart rhythm, called fibrillation. These instances are generally identifiable by the victim's immediate loss of pulse, loss of consciousness and a cessation of breathing.

Sudden cardiac arrest has been attributed to over 350,000 deaths each year in the United States, making it one of the country's leading medical emergencies. World-wide, sudden cardiac arrest has been attributed to a much larger number of deaths each year. Unless medical intervention is initiated, sudden cardiac arrest will lead to death within a matter of minutes. With rapid intervention, the survival rate for sudden cardiac arrest can be as high as 40%.

There are four critical components of medical treatment that must be administered to a victim of sudden cardiac arrest: (1) early access to emergency care; (2) early cardiopulmonary resuscitation to keep the blood oxygenated and flowing to the victim's brain and other vital organs; (3) early defibrillation (the application of an electrical shock to the heart) to restore the heart's regular rhythm; and (4) early access to advanced medical care. When a person is experiencing sudden cardiac arrest, the electrical activity within the heart becomes chaotic. An electric shock from a defibrillator can reorganize the electrical impulses to allow coordinated pumping action to resume. To administer this shock, special pads from a machine called a defibrillator are placed on the victim's chest, and an electric shock is sent through the victim's body from one pad to another. As used herein, the term "pads" will include both pads and paddles.

If prompt cardiopulmonary resuscitation is followed by defibrillation within about four minutes, the victim's chances of surviving sudden cardiac arrest can approach or exceed 40%. Prompt administration of defibrillation within the first critical minutes is considered one of the most important components of emergency medical treatment for preventing death from sudden cardiac arrest.

Since prompt defibrillation is critical to survival, portable defibrillators have been developed that can be carried to the victim's location to defibrillate the victim prior to reaching a hospital. These portable defibrillators, like other sensitive electronic equipment, occasionally can malfunction or otherwise be unable to operate properly. While malfunctioning of typical electronic equipment is inconvenient, a malfunctioning defibrillator can be fatal to the patient in sudden cardiac arrest. Accordingly, it would be advantageous to have a defibrillator that could minimize the effects of any malfunction.

SUMMARY OF THE INVENTION

The present invention is a defibrillator having one or more redundant systems each including functionally interchangeable components from which one such component is selected for current operation. As used herein, the term "component" refers to any operational element of the defibrillator, and may include, for example, circuits, processors, mechanical components, subsystems or any combination thereof. Manual or automatic selection of one operational component in each redundant system is made to form an operational defibrillator. Preferably, such selection is based on a real-time evaluation of the operational integrity of all operational components in a redundant system. In one embodiment, a default operational component is selected for each redundant system. The default operational component is initially selected to be put into operation unless or until a malfunction occurs. Such real-time evaluations may be performed by monitoring systems within a selection system, by an external test system within or external to the defibrillator, or by self-test mechanisms internal to the operational components. Factors such as user preferences, default component assignment, and predetermined arrangements of operational component combinations may be included in the selection determination along with the operational integrity of each operational component. Significantly, a defibrillator implemented in accordance with the present invention provides for the selection of a combination of available, operational components to insure the continued availability of an operational defibrillator despite the presence of malfunctioning or otherwise degraded components. If certain, non-critical components fail with no functionally interchangeable components available, then the redundant system comprising such a failed component is not made operational. The remaining systems of the defibrillator may still be implemented to form a defibrillator sufficient for defibrillation yet lacking the capability to implement the functions allocated to the malfunctioning, degraded or otherwise absent redundant system.

As used herein, operational components are considered to be "functionally interchangeable" when the components perform the same or similar operations in the same or similar manner. Not every operation performed by one component of a redundant system is necessarily performed by all other components of that redundant system. For example, certain ancillary operations not affecting component performance may not be identically performed by all components of a redundant system. Also, variations may exist between redundant components due to, for example, the type of defibrillators for which they were designed, different component manufacturers, type of implementation (hardware, firmware, or software), and the like. In addition, redundant systems may be logically or physically associated to form a larger redundant system, referred to herein as redundant assemblies. An assembly may include, for example, all operations systems or all user interface components.

A number of aspects of the invention are summarized below, along with different embodiments that may be implemented for each of the summarized aspects. It should be understood that the embodiments are not necessarily inclusive or exclusive of each other and may be combined in any manner that is non-conflicting and otherwise possible. It should also be understood that these aspects of the invention are exemplary only and are considered to be non-limiting.

In one aspect of the invention a defibrillator including one or more redundant systems each including at least two functionally interchangeable operational components is disclosed. A selection system of the defibrillator is operationally coupled to the redundant systems and is constructed and arranged to select one of the operational components from each of the redundant systems for current operation in the defibrillator. The selection is based at least on a relative operational integrity of each of the operational components within each redundant system.

In one embodiment, the selection system includes an operational status monitor constructed and arranged to generate an indication of an operational integrity of each of the operational components. The operational status monitor may be distributed within each of the operational components of each of the redundant systems. A selection controller determines which operational component is to be selected for current operation based on the operational integrity of the operational components. A switching control system, responsive to the selection controller, dynamically configures the redundant system such that the selected operational component is currently operational and the operational components of the redundant system other than the selected operational component are not currently operational. The selection system may also be responsive to externally-provided selections, such as manual entries made by a user of the defibrillator.

The redundant systems may include, for example, a high voltage charging circuit for storing energy from a power source for subsequent delivery to pads of the defibrillator, a power supply, coupled to a power source, for supplying operational power to other components of the defibrillator, an ECG unit for monitoring a patient connected to electrodes of the defibrillator, an audio recording and playback unit for receiving audio input from a microphone, and for presenting audio output through a speaker of the defibrillator, etc.

In alternative embodiments, the operational components of each redundant system are logically distributed across redundant assemblies. Each redundant assembly includes operational components that are functionally interchangeable with operational components of other redundant assemblies. In such embodiments, the selection system selects one of the redundant assemblies for current operation in the defibrillator. The redundant assemblies may take on any desired arrangement. For example, the defibrillator may include redundant assemblies each comprising all critical components of the defibrillator. The operational redundant assembly may include some of the noted operational components, such as a high voltage charging circuit, a defibrillation control unit, and an ECG unit.

In another aspect of the invention a defibrillator including one or more redundant systems each including at least two operational components that are functionally interchangeable with the other operational components of that redundant system. Only one operational component of each redundant system is selected for operational based on a relative operational integrity of each of the operational components in that redundant system. The defibrillator includes a selection system for making such a selection. The selection system includes an operational status monitor constructed and arranged to generate an indication of the operational status of the operational components. The selection system also includes a selection controller that determines which of the operational components are to be selected for current operation in the defibrillator based on an operational integrity derived from at least the status information provided by the monitor. Preferably, the selection system also includes a switching control system that dynamically configures each of the redundant systems such that the selected operational component is currently operational and the operational components of the redundant system other than the selected operational component are not currently operational.

In another aspect of the invention, a method for providing an operational defibrillator is disclosed. The method includes 1) providing a defibrillator including one or more redundant systems each including at least two functionally interchangeable operational components; and 2) selecting one of the operational components from each of the one or more redundant systems for current operation on the defibrillator.

The selecting of the operational components includes a) determining an operational integrity of the operational components; b) determining which of the operational components is to be selected for current operation in the defibrillator based on at least the operational integrity of the operational components; and, preferably, c) dynamically configuring the redundant system such that the selected operational component is currently operational and the operational components of the redundant system other than the selected operational component are not currently operational.

Various embodiments of the present invention provide certain advantages and overcome certain drawbacks of the conventional defibrillators. Not all embodiments of the invention share the same advantages and those that do may not share them under all circumstances. This being said, embodiments of the present invention provide numerous advantages including the noted advantage of increasing the operational availability of the defibrillator regardless of substantial component failures, malfunctions, degradation or unavailability. Specifically, embodiments of the present invention allow for real-time formation of an operational defibrillator from redundant components implemented therein. Further features and advantages of the present invention as well as the structure and operation of various embodiments of the present invention are described in detail below with reference to the accompanying drawings.

BRIEF DESCRIPTION OF THE DRAWINGS

This invention is pointed out with particularity in the appended claims. The above and further advantages of this invention may be better understood by referring to the following description when taken in conjunction with the accompanying drawings, in which:

DETAILED DESCRIPTION

The present invention relates to an external defibrillator having redundant components that enable the defibrillator to operate when one or more components of the defibrillator malfunctions. Selection of defibrillator components for redundancy can be made in accordance with various criteria. For example, redundancy may be provided for only those components that fail frequently, for all operational components, for all user interface and operational components, etc. Optionally, the redundant components may be physically or logically gathered into separate redundant defibrillator subsystems. Alternatively, the components may be independently selectable for operation and not preferentially predisposed to be selected with other related or unrelated components. A selection controller is provided to select for current operation one of the physical or logical defibrillators. The controller takes into account whether the physical or logical defibrillator or its components are operational in making this determination.

Optionally, the components can be grouped into a main defibrillator and a back-up defibrillator. The controller in this case can receive inputs to determine if the main defibrillator is operational. If it is, the controller enables the main defibrillator for current operation; if not, the back-up defibrillator is enabled for current operation. The controller may also select individually components from the main defibrillator and back-up defibrillator to form an operational defibrillator when neither the main defibrillator nor back-up defibrillator is itself functional.

Selection of one defibrillator or a subset of components may be preferential or non-preferential. Where preferential, the controller can be configured to select from a first group of components ideally enabled for current operation and enable redundant components for current operation only when the first group or components of the first group are not operational.

The controller may determine the operability of the defibrillators or components thereof at any of a number of points in time. For example, the controller may: (1) select in advance components for future operation during periodic maintenance or self tests while in standby mode; (2) select one of the defibrillators or a set of components for current operation when the defibrillator is first turned on; and (3) select one of the defibrillators or a set of components dynamically during operation of the defibrillator upon determination that one or more components is malfunctioning. Periodic refresh or monitoring signals, either internally generated by the components or responded to by the components, may be used to poll the components and defibrillators to determine their operability.

Figure 1:
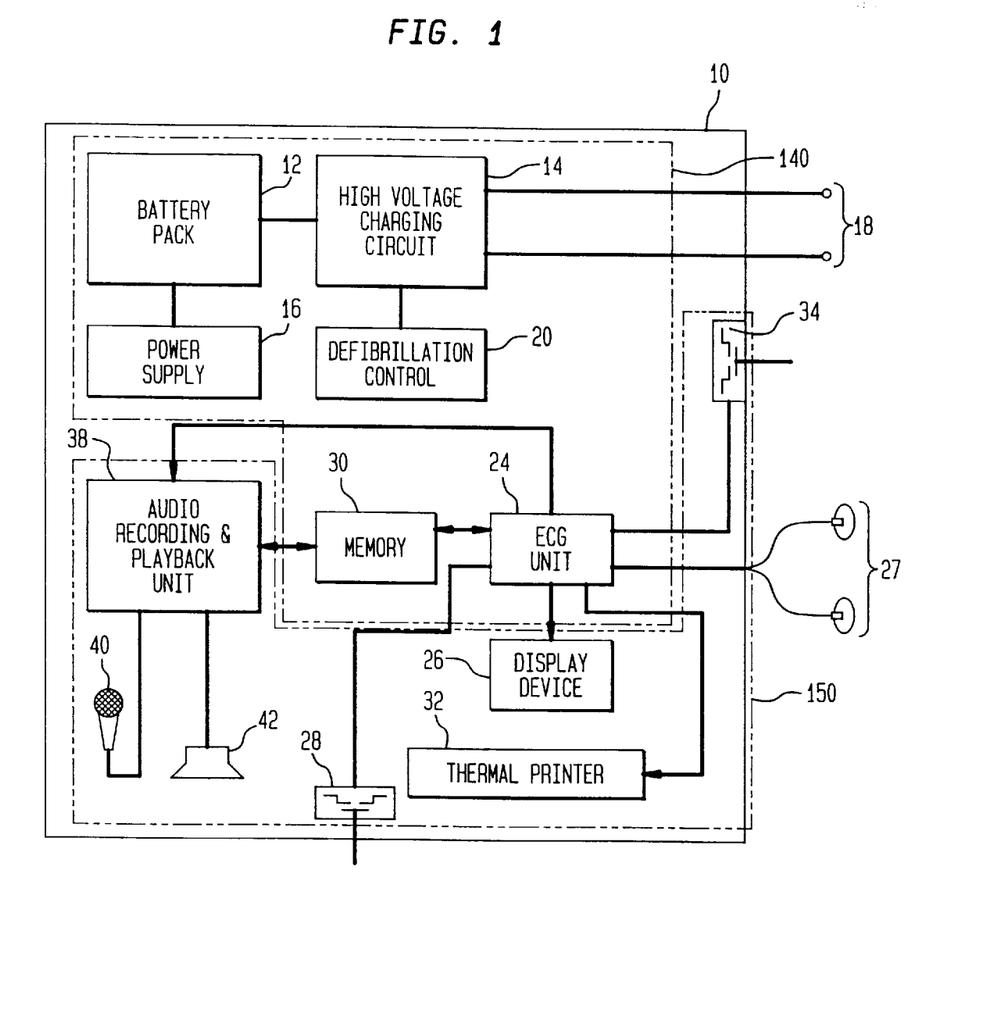
FIG. 1 is a functional block diagram of a conventional defibrillator.

With reference now to the figures and in particular with reference to FIG. 1, there is illustrated a block diagram of a defibrillator in accordance with the present invention. Defibrillator 10 includes a rechargeable battery pack 12, which supplies power to defibrillator 10. As a battery-powered device, defibrillator 10 is highly portable and therefore suitable for pre-hospital (emergency) use. Battery pack 12 preferably includes one or more nickel-cadmium (NiCd), lithium, zinc-air, or lead-acid batteries capable of providing power for several hours of operation. As illustrated, battery pack 12 is electrically coupled to high voltage charging circuit 14 and supplies charge to a large capacitor contained within high voltage charging circuit 14 utilized to store the large charge required to defibrillate an arrhythmic patient. Battery pack 12 is further electrically coupled to power supply 16, which supplies operational power to the individual components within defibrillator 10. High voltage charging circuit 14 is electrically connected to a pair of pads 18 utilized to deliver a defibrillating shock to the patient. The delivery of the defibrillating shock to the patient by a high voltage charging circuit 14 is controlled by defibrillation controller 20.

Still referring to FIG. 1, defibrillator 10 further includes electrocardiogram (ECG) unit 24, which controls the monitoring functions of defibrillator 10. From the following description of ECG unit 24, those skilled in the art will appreciate that ECG unit 24 may be implemented utilizing a conventional microprocessor and support circuitry, or alternatively, an application-specific integrated circuit (ASIC). ECG unit 24 receives ECG data from a patient through chest electrodes 27, which are preferably coated with a conductive gel to establish a good electrical contact with the patient. The ECG data received from the patient is temporarily buffered in an ECG data buffer within ECG unit 24 and displayed in real-time to the operator of defibrillator 10 within display device 26. The ECG data is preferably displayed in the form of a conventional ECG waveform trace, and may be displayed in conjunction with additional information extracted from the ECG data, such as the patient's instantaneous pulse rate.

ECG unit 24 is further coupled to user controls 28, 34, such as a "mark" button which is depressed by an operator to store ECG data of interest within memory 30. During treatment of a patient, the operator typically utilizes mark button 28 to record segments of ECG data sensed before and after the administration of drugs, the delivery of shocks, and other major treatment events. The collection of ECG data segments stored in memory 30 by the operator during treatment of a patient, known as a "code" summary, can be printed by the operator of defibrillator 10 on thermal printer 32 by depressing review button 34. In addition, the ECG unit 24 could store all of the patient's ECG data sensed during treatment within memory 30 in conjunction with a list of marked events for later use. Alternatively, ECG unit could automatically mark events preselected by the operator, such as the delivery of shocks.

ECG unit 24 is further coupled to audio recording and playback unit 38 by control signals 36. Audio recording and playback unit 38 receives audio input from microphone 40 and presents audio output to the operator of defibrillator 10 through speaker 42. In response to user input via control 28 or 34, the audio recording and playback unit 38 sense audio data via microphone 40, digitizes the audio data, and stores the audio data within memory 30. As will be appreciated by those skilled in the art, the audio data can be compressed prior to storage utilizing any of a number of well-known data compression algorithms in order to minimize the amount of memory 30 required to store the audio data. The audio data may be stored within memory 30 in association with the ECG data recorded in response to the same depression of button 28. The audio data may also be stored by audio recording and playback unit 38 on magnetic tape, magnetic disc or optical recording media.

To facilitate the memory 30, memory 30 preferably comprises a removable and portable data storage device, such as a PCMCIA (Personal Computer Memory Card International Association) memory card; however, memory 30 can alternatively be implemented as a nonremovable memory. In addition, defibrillator 10 preferably includes an infrared serial port or other data communication means (not illustrated) to enable the contents of memory 30 to be downloaded directly to a computer for review and analysis.

The components of defibrillator 10 illustrated in FIG. 1 have been grouped roughly into two categories: operational components 140 and user interface components 150. The operational components generally include components that sense ECG signals, analyze the signals, and deliver an electrical shock to the victim. In the illustrated embodiment, the operational components 140 include the battery pack 12, high voltage charging circuit 14, power supply 16, defibrillation controller 20, ECG unit 24 and memory 30.

The user interface components generally include components that receive input from the user or provide information to the user. In the illustrated embodiment, the user interface components 150 include display device 26, thermal printer 32, user interface controls 28, 34, audio recording and playback unit 38, microphone 40 and speaker 42. The delineation or grouping of components into operational components 140 and user interface components 150 is one way of dividing the components of the defibrillator into more than one subset. Additional groupings are equally possible.

Figure 2A:
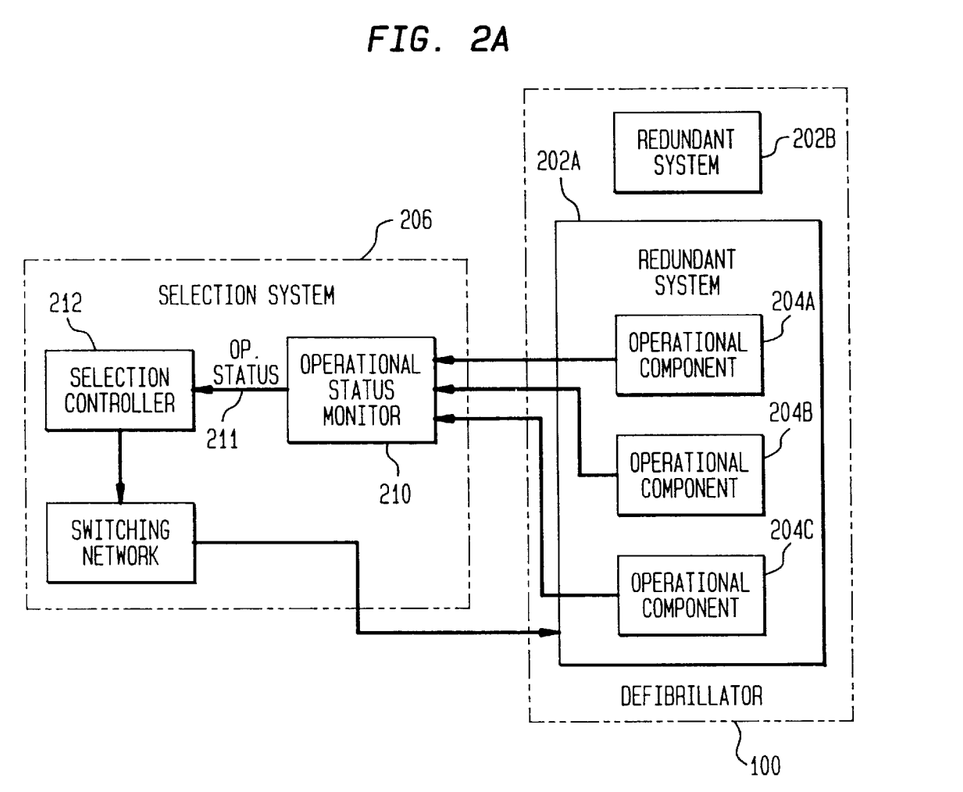
FIG. 2A is a functional block diagram of a selection system according to one embodiment of the present invention.

FIG. 2A is a functional block diagram of one embodiment of the selection system of the present invention. As shown therein, the defibrillator 100 includes a redundant system 202 that includes three functionally interchangeable operational components 204A–204C from which one operational component 204 is selected for current operation by the selection system 206. As used herein, the term "component" refers to any operational element of the defibrillator 100, and may include, for example, circuits, processors, mechanical components, subsystems or any combination thereof. A second redundant system 202B performing functions different than those performed by redundant system 202 is also included in the defibrillator 100. Although not shown, redundant system 202B also includes two or more functionally interchangeable operational components. Manual or automatic selection of one component 204 in each redundant system 202 is made to form an operational defibrillator 100. Manual selection may be made using a switch or selection from a user interface.

As used herein, operational components are considered to be "functionally interchangeable" when the components perform the same or similar operations is the same or similar manner. Not every operation performed by one component of a redundant system is necessarily performed by the other components. For example, certain ancillary operations not affecting component performance may not be identically performed by all components of a redundant system. Also, variations may exist between redundant components due to, for example, being designed for implementation in different types of defibrillators, different component manufacturers, type of implementation (hardware, firmware, or software), and the like. In addition, redundant systems may be logically or physically associated to form a larger redundant system, referred to herein as assemblies. An assembly may include, for example, all operations systems or all user interface components. Any system or component of the defibrillator 100 may be configured as a redundant system 202. For example, the high voltage charging circuit, power supply, ECG unit or audio recording and playback unit may be a redundant system 202. For example, redundant system 202A may be the high voltage charging circuit, and include three such circuits 204A–204C.

The one operational component from each of the redundant systems 202 may be logically grouped into redundant assemblies. Each redundant assembly is therefore functionally interchangeable with other redundant assemblies. In such embodiments, the selection system 206 selects one of the redundant assemblies for current operation in the defibrillator 100. Such redundant assemblies may take on any desired arrangement. For example, as will be described in detail below, the defibrillator 100 may include an operational redundant assembly and a user interface redundant assembly.

In the illustrative embodiment, the selection system 206 includes an operational status monitor 210, a selection controller 212 and a switching control system 214. The operational status monitor 210 is constructed and arranged to generate operational status information of each of the operational components 204 of each of the redundant systems 202. The operational status monitor 210 may be located locally or distributed within each of the operational components 204. Thus, in some embodiments, the operational status monitor 210 is not as shown in FIG. 2A but is distributed at self-test modules on each of the operational components 204. In either of these or other embodiments, the operational status monitor 210 generates operational status information 211 that identifies the operational status of each of the operational components 204. The operational status information may be of any form and of any degree of specificity, depending on the type of operational component and its ability to test and evaluate systems, subsystems, components, etc. The operational status information 211 may be provided to the selection controller 212 in any form as well, such as dedicated signals, data transferred over a bus, shared memory or the like.

The selection controller 212 is constructed and arranged to determine which of the operational components 204 is to be selected for current operation in the defibrillator 100 based on a relative operational integrity of the operational components 204. Preferably, such a determination is based on a real-time evaluation of a relative operational integrity of all operational components 204 in a redundant system 202. Other factors may be considered in addition to the relative operational status of the operational components 204, other factors may be considered. For example, factors such as user preferences, default component assignment, and predetermined arrangements of operational component combinations may be included in the selection determination along with the operational integrity of operational components 204 of each redundant system 202. The selection controller 212 may be implemented in hardware, firmware, software or any combination thereof.

The switching control system 214 is responsive to the selection controller 212, and is constructed and arranged to dynamically configure each redundant system such that the selected operational component is currently operational and the operational components of the redundant system other than the selected operational component are not currently operational. The switching network 214 may be nothing more than an enable/disable signal or flag to the selected operational component. In other embodiments, the switching network 214 may include switches that control the application of power generated by certain components so that it is received by the appropriate operational component 204. Thus, although it is shown as a single unitary element of selection system 206, switching network 214 may be distributed throughout redundant system 202 to control the selection of operational components 204.

Figure 2B:
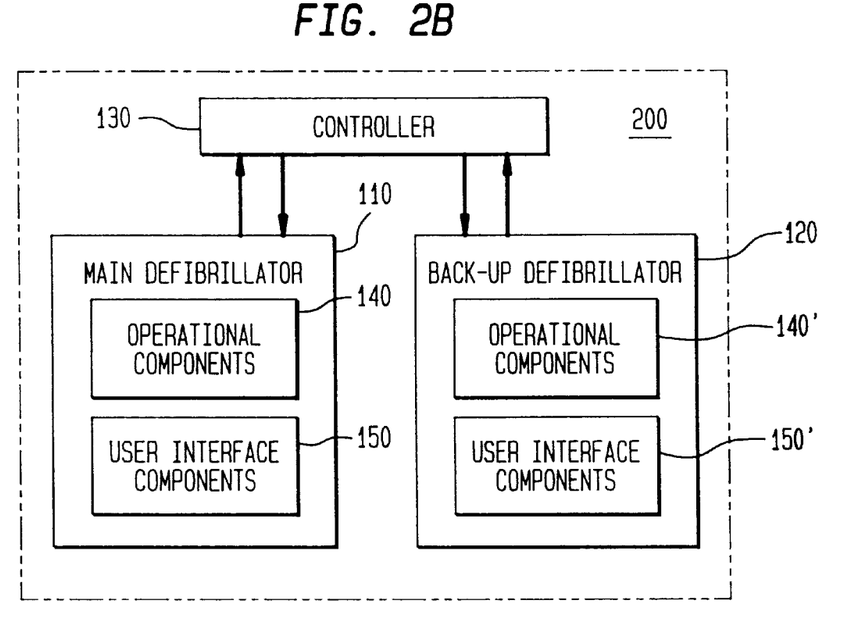
FIG. 2B is a functional block diagram of a defibrillator according to a first embodiment of the present invention.

In the exemplary embodiment illustrated in FIG. 2B, defibrillator 100 is provided with a two redundant assemblies 208 each having systems that are functionally interchangeable with the other. As shown, these redundant assemblies are a main defibrillator 110 and a back-up defibrillator 120. In this embodiment, the main defibrillator 110 and back-up defibrillator 120 contain redundant operational components 140 as well as redundant user interface components 150. In this illustrative embodiment, operational status monitor 210 is distributed between the main defibrillator 110 and the back-up defibrillator 120 and switching network 214 are shown as two signal lines traveling from a selection controller 130 to the defibrillators 110, 120.

The selection controller 130 is provided to select one of the main defibrillator 110 and the back-up defibrillator 120 for operation, depending on status signals provided by the operational components 140, 140' and, optionally, the user interface components 150, 150'. The controller 130 processes the received signals to select one of the defibrillators that is most likely to be operational, and enables the selected defibrillator for current operation.

Not all components, systems, etc., are required to be redundant systems. For example, in the embodiment illustrated in FIG. 3, the defibrillator 100 is provided with a main defibrillator 110 and a back-up defibrillator 120. In this embodiment, however, a single set of user interface components 150 are provided. The main defibrillator 110 and back-up defibrillator 120 in this embodiment thus contain only redundant operational components 140, 140'. A selection controller 130 is provided to select one of the main defibrillator 110 and the back-up defibrillator 120 for operation, depending on status signals provided by the operational components 140, 140'. The controller 130 processes the received signals to select one of the defibrillators that is most likely to be operational, and enables the selected defibrillator for current operation.

Figure 3:
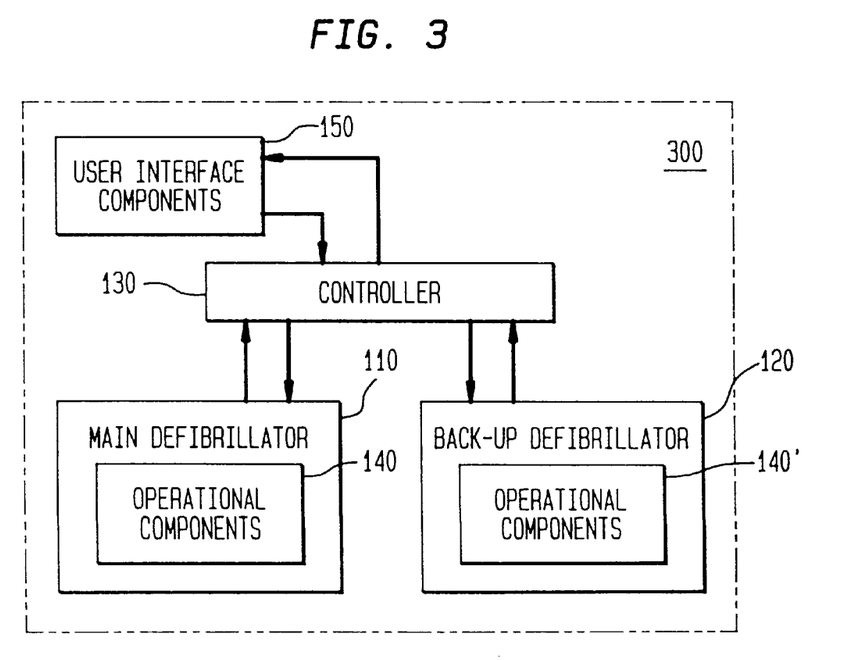
FIG. 3 is a functional block diagram of a defibrillator according to a second embodiment of the present invention.

Redundant user interface controls is advantageous, since an malfunction may occur, for example, in the display of the defibrillator. Operating the defibrillator without a display would present additional challenges to the operator, but may be made possible through audio prompts and via reception of audio commands, by communicating with a peripheral device via an I/O port, etc. Accordingly, redundancy of the user interface components may not be essential to operation of the defibrillator. Thus, to minimize the cost of the portable defibrillator, the embodiment illustrated in FIG. 3 provides for redundancy of only the operational components. By contrast, FIG. 2 provides redundancy for all components so that if any component of the defibrillator malfunctions, the other defibrillator can be used. An intermediate position may be taken as well. For example, it may be possible to provide redundancy of some operational components and some user interface components without providing redundancy of all operational components or all user interface components. Likewise, it may not be necessary to provide redundancy for the battery pack, since spare batteries are typically carried along with the defibrillator.

Figure 4:
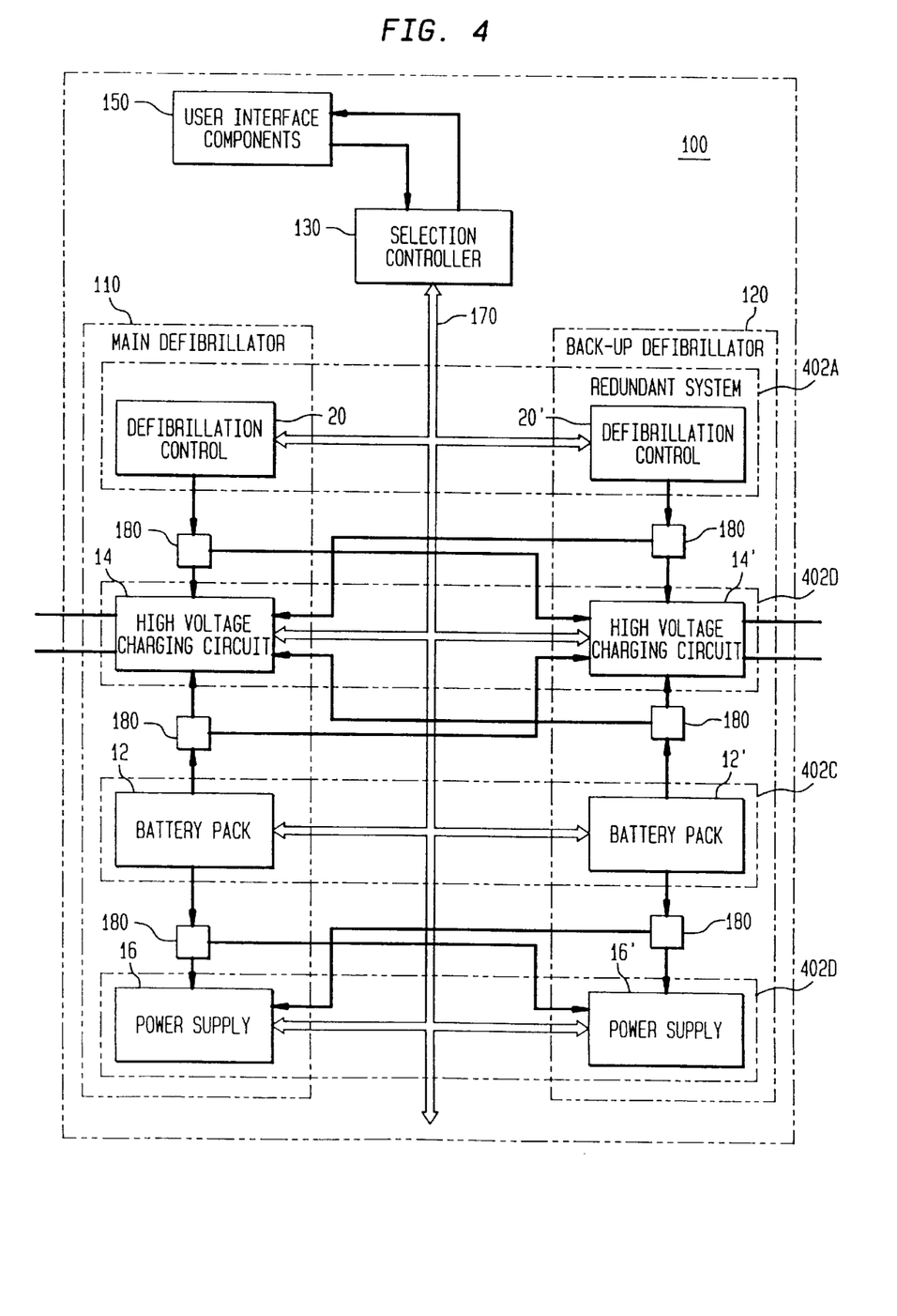
FIG. 4 is a functional block diagram of a defibrillator according to a third embodiment of the present invention.

Another embodiment of the defibrillator is illustrated in FIG. 4. In this embodiment, two functionally interchangeable operational components are illustrated in each of four redundant systems 402A–402D. One operational component is selected for current operation from each redundant system 402 based on any number of factors, such as those noted above. It should be understood that this embodiment is not limited in this regard, and the concepts disclosed below apply equally where redundancy of additional or fewer components is provided.

In the embodiment of FIG. 4, the defibrillator 10 has also been logically divided into two redundant assemblies: a main defibrillator 110 and a back-up defibrillator 120. However, in the embodiment of FIG. 4, the selection controller 130 individually selects operational components from each of the redundant systems 402A–402D rather than selection either the main or back-up defibrillator. This is advantageous, for example, where one or more components of both the main defibrillator and back-up defibrillator malfunction at the same time. By selecting individually components from a plurality of redundant systems, the selection controller 130 can piece together an operational defibrillator to ensure that the defibrillator 10 will function as directed by the user.

For example, the selection controller 130 of defibrillator 10 may determine that defibrillation control 20 and high voltage charging circuit 14' are malfunctioning. If individual selection of redundant components was not possible, the defibrillator 10 would not be able to defibrillate a victim, even though there are two complete sets of complimentary operational components. By providing for individual selection, however, the controller 130 can, for example, select for operation defibrillation control 20', high voltage charging circuit 14, battery pack 12 and power supply 16 to form a complete defibrillator. Likewise, if one of the battery packs is low or is taking a long time to charge the high voltage charging circuit 14, the controller 130 can either switch to the redundant battery pack 12' or can enable simultaneously both battery pack 12 and battery pack 12'.

In the exemplary embodiment illustrated in FIG. 4, the controller 130 is connected to the components of the main defibrillator 110 and back-up defibrillator 120 via a bus 170. The controller 130 uses the bus 170 to receives status signals from the defibrillator components and to send enable signals to the defibrillator components. Switches 180 are provided to enable selective interconnection of components from main defibrillator 110 and back-up defibrillator 120 to allow components from the two defibrillators to work together to form an operational defibrillator. This may be advantageous where multiple components of the defibrillator malfunction simultaneously. Optionally, the switches 180 can be logically or physically associated with the defibrillator components such that communication with the switches 180 is not required independent of communication with defibrillator components. In FIG. 4, the designation of defibrillator components as belonging to the main defibrillator or back-up defibrillator has less significance since the components in this exemplary embodiment are individually selectable. While a bus has been illustrated as interconnecting the controller 130 with the individual components, dedicated control lines, shared memory, and any number of other known devices for facilitating communication between components could equivalently be used.

In the embodiment illustrated in FIG. 4, switches 180 have been provided on the outputs of the defibrillation control units 20, 20', battery pack 12, 12' and power supply 16, 16'. The switches may be integral to these components or may be interposed between the various components as illustrated. The switches 180 are controlled by the controller 130 via bus 170 to facilitate enabling one or more components of the defibrillator for operation. Other ways of enabling the components for operation would be readily apparent to a person of ordinary skill in the art.

Figure 5:
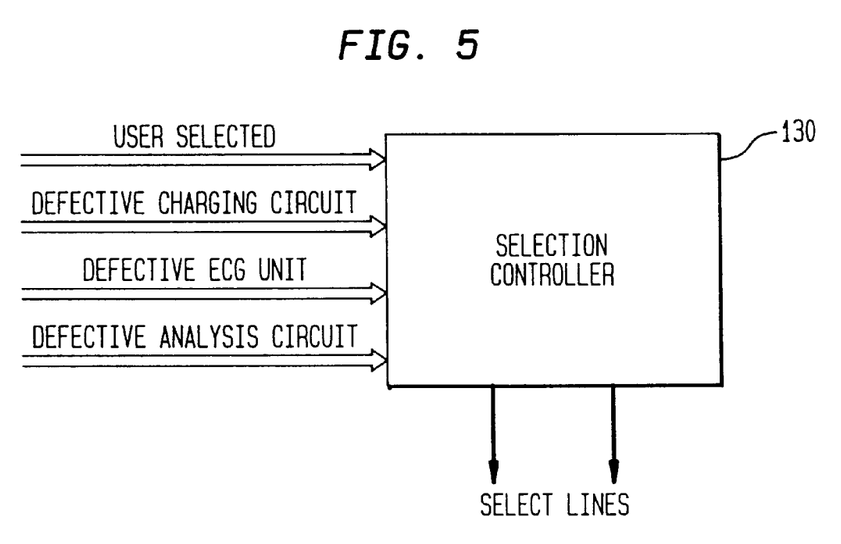
FIG. 5 is a schematic block diagram of a controller for use in the defibrillators illustrated in FIGS. 2B through 4.

The controller 130 may receive inputs indicative of the status or health of the subsystems from multiple components of the defibrillator 100. Thus, for example as illustrated in FIG. 5, the controller 130 may receive input directly from the user, from operational components 140 of both the main defibrillator 110 and the back-up defibrillator 120, or from the interface components 150. As illustrated in FIG. 5, the inputs could include an indication that one of the defibrillators includes, e.g., a defective charging circuit, a defective ECG unit or a defective analysis circuit. Likewise, the controller 130 could receive inputs indicating that the thermal printer, microphone, speaker or any other component is defective. The controller 130 can use this input during selection of one of the main defibrillator 110 and back-up defibrillators for operation. Optionally, where the input indicates that a non-essential component has malfunctioned, the defibrillator 100 may choose to warn the operator. Warning the operator can enable the operator to elect to use a different defibrillator or to operate the defibrillator without the non-essential component. Non-essential components in this regard can include any component that is not required to enable the defibrillator to administer a defibrillatory shock to the victim.

Figure 6:
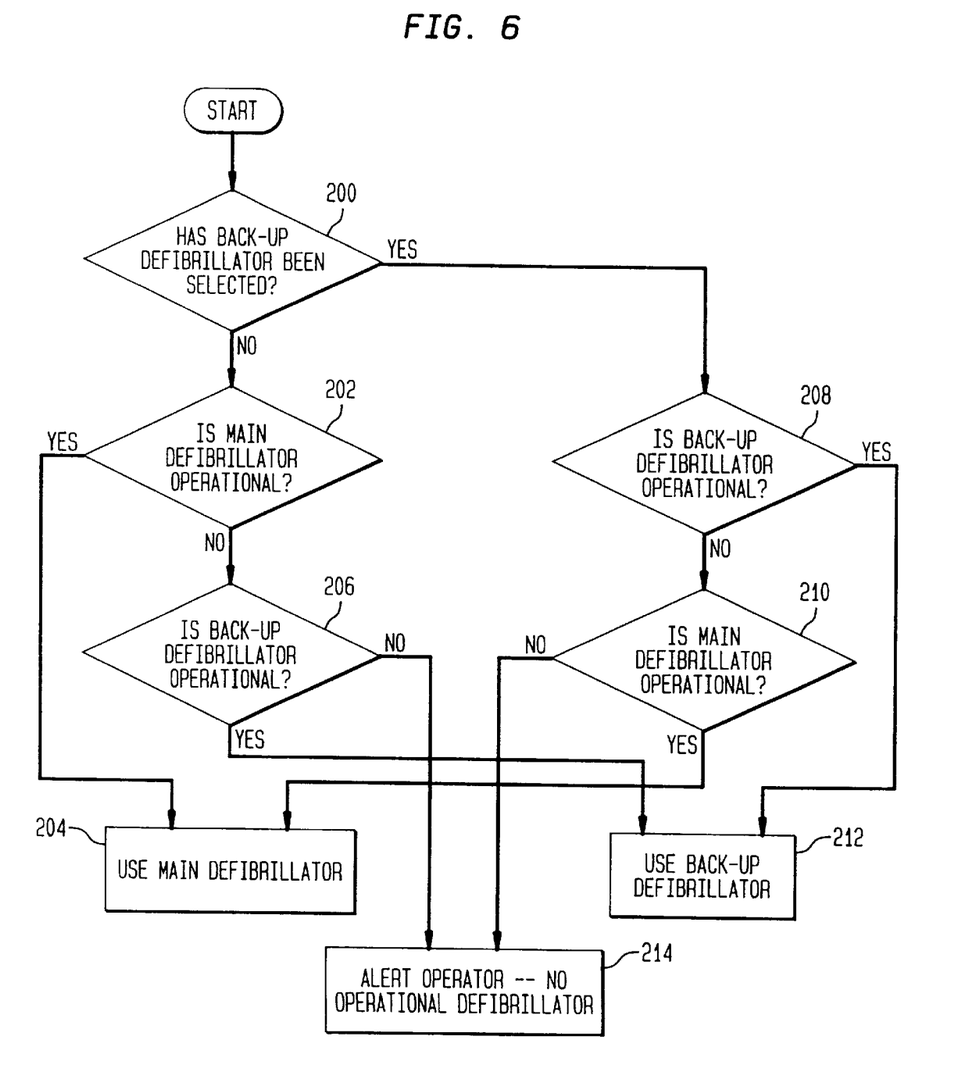
FIG. 6 is a flow chart illustrating an exemplary process of selecting between a main defibrillator and a back-up defibrillator in accordance with one embodiment of the present invention.

FIG. 6 illustrates functions performed by software running on controller 130 if the controller 130 is implemented as a microprocessor, or functions performed by the hardware comprising controller 130 where the controller 130 is implemented as an ASIC. As shown in FIG. 6, the controller 130 first determines if the user has selected the back-up defibrillator for operation 200. Optionally, this step may be avoided and the defibrillator may be preprogrammed to first evaluate operational characteristics of the main defibrillator and then to evaluate operational characteristics of the back-up defibrillator, or vise versa.

The controller 130 then determines if the main defibrillator is operational 202. If the main defibrillator is operational, the controller 130 will select the main defibrillator and cause the main defibrillator to be used to defibrillate the victim 204. If the main defibrillator is not operational, the controller 130 will determine if the back-up defibrillator is operational 206. If the back-up defibrillator is operational, the controller 130 will select the back-up defibrillator and cause the back-up defibrillator to be used during the defibrillation process 212. Analogously, if the back-up defibrillator has been initially selected at 200, the controller 130 will first look to see if the back-up defibrillator is operational 208 and then, if necessary, look to see if the main defibrillator is operational 210. In either case, if the controller 130 determines that both the main defibrillator and the back-up defibrillator are not functional, it will alert the operator that the defibrillator cannot be operated safely and turn itself off 214. Alternatively, if the defibrillator is provided with a system such as that illustrated in FIG. 4, the defibrillator could attempt to piece together functional components from the main and back-up defibrillators prior to notifying the operator that malfunctions prevent the defibrillator from operating.

Although the concepts disclosed in this application has been explained with respect to a portable external defibrillator, the principles described herein could easily be applied to other medical devices or electronic equipment used by emergency medical personnel, such as EKG monitors, $SpO_2$ monitors, etc.

It should be understood that various changes and modifications of the embodiments shown in the drawings and described in the specification may be made within the spirit and scope of the present invention. Accordingly, it is intended that all matter contained in the above description and shown in the accompanying drawings be interpreted in an illustrative and not in a limiting sense. The invention is limited only as defined in the following claims and the equivalents thereto.

What is claimed is:

1. A defibrillator comprising:
   one or more redundant systems each comprising at least two functionally interchangeable operational components; and
   a selection system operationally coupled to said one or more redundant systems, constructed and arranged to select one of said operational components from each of said one or more redundant systems for current operation defibrillator based on at least on an operational integrity of each of said operational components so as to form a circuit for delivering a shock to a patient via electrical leads.

2. The defibrillator of claim 1, wherein said one or more redundant systems comprises:
   a high voltage charging circuit for storing energy from a power source for subsequent delivery to pads of the defibrillator.

3. The defibrillator of claim 2, wherein said one or more redundant systems further comprises:
   a power supply, coupled to a power source, for supplying operational power to other components of the defibrillator.

4. The defibrillator of claim 3, wherein said one or more redundant systems comprises:
   an ECG unit for monitoring a patient connected to electrodes of the defibrillator.

5. The defibrillator of claim 4, wherein said one or more redundant systems comprises:
   an audio recording and playback unit for receiving audio input from a microphone, and for presenting audio output through a speaker of the defibrillator.

6. The defibrillator of claim 5, wherein said selection system is responsive to externally-provided selections.

7. The defibrillator of claim 6, wherein externally-provided selections are manual entries made by a user of the defibrillator.

8. The defibrillator of claim 1,
   wherein said one or more redundant systems are logically divided into redundant assemblies each including redundant systems that are functionally interchangeable with redundant systems of other redundant assemblies,
   wherein said selection system selects one of said redundant assemblies for current operation in the defibrillator.

9. The defibrillator of claim 8, wherein said redundant assemblies comprises:
   an operational redundant assembly including a high voltage charging circuit, a defibrillation control, and an ECG unit; and
   a user interface redundant assembly including a display device, an audio recording and playback unit, a printer, a speaker and a microphone.

10. The defibrillator of claim 8,
    wherein said redundant assemblies are logically grouped to form a main defibrillator and a back-up defibrillator,
    wherein said selection system selects one of said main defibrillator and said back-up defibrillator for current operation in the defibrillator.

11. The defibrillator of claim 1, wherein said selection system comprises:
    an operational status monitor constructed and arranged to generate an indication of said operational integrity of said operational components;
    a selection controller constructed and arranged to determine which of said operational components is to be selected for current operation in the defibrillator based on said operational integrity of said operational components; and
    a switching control system, responsive to said selection controller, constructed and arranged to dynamically configure said redundant system such that said selected operational component is currently operational and said operational components of said redundant system other than said selected operational component are not currently operational.

12. The defibrillator of claim 11, wherein said an operational status monitor is distributed within each of said operational components of each of said one or more redundant systems.

13. A defibrillator comprising one or more redundant systems each comprising at least two functionally interchangeable operational components of which only one such operational component is selected for operation based on a relative operational integrity of each of said operational components.

14. The defibrillator of claim 13, wherein the defibrillator comprises a selection system for making said selection of said operational component for operation, said selection system comprising:

an operational status monitor constructed and arranged to generate an indication of said operational integrity of said operational components; and a selection controller constructed and arranged to determine which of said operational components is to be selected for current operation in the defibrillator based on said operational integrity of said operational components.

15. The defibrillator of claim 14, wherein selection system further comprises:

a switching control system, responsive to said selection controller, constructed and arranged to dynamically configure said redundant system such that said selected operational component is currently operational and said operational components of said redundant system other than said selected operational component are not currently operational.

16. A method for providing an operational defibrillator, comprising:

1) providing a defibrillator comprising one or more redundant systems each comprising at least two functionally interchangeable operational components; and 2) selecting one of said operational components from each of said one or more redundant systems for current operation on the defibrillator.

17. The method of claim 16, wherein said selecting comprises:

a) determining an operational integrity of said operational components;

b) determining which of said operational components is to be selected for current operation in the defibrillator based on at least said operational integrity of said operational components.

18. The method of claim 17, wherein said selecting further comprises:

c) dynamically configuring said redundant system such that said selected operational component is currently operational and said operational components of said redundant system other than said selected operational component are not currently operational.

19. A defibrillator comprising:

a plurality of operational components that combine to form a circuit to deliver a shock to a patient through a pair of pads placed externally on the patient;

at least one redundant component corresponding to at least one of the plurality of operational components; and a selection unit that when an operational component, having a corresponding redundant component, is determined to be malfunctioning, functionally disconnects the malfunctioning operational component from the circuit and switches the corresponding redundant component into the circuit.

20. A defibrillator, as set forth in claim 19 wherein the plurality of operational components and the at least one redundant component are interconnected by a bus.

* * * * *